US007354901B2

(12) United States Patent
Rudolph et al.

(10) Patent No.: US 7,354,901 B2
(45) Date of Patent: Apr. 8, 2008

(54) PRODUCTION OF RECOMBINANT BMP-2

(75) Inventors: Rainer Rudolph, Dr.-Hans-Litten-Str. 28, 06120 Halle (DE); Elisabeth Schwarz, Dr.-Hans-Litten-Str. 28, 06120 Halle (DE); Gerhard Herr, Wetzlar (DE); Frank Hillger, Dessau (DE)

(73) Assignees: Rainer Rudolph, Halle (DE); Elisabeth Schwarz, Halle (DE)

( * ) Notice: Subject to any disclaimer, the term of this patent is extended or adjusted under 35 U.S.C. 154(b) by 552 days.

(21) Appl. No.: 10/433,077

(22) PCT Filed: Nov. 27, 2001

(86) PCT No.: PCT/EP01/13840

§ 371 (c)(1),
(2), (4) Date: May 29, 2003

(87) PCT Pub. No.: WO02/44203

PCT Pub. Date: Jun. 6, 2002

(65) Prior Publication Data

US 2004/0018595 A1 Jan. 29, 2004

(30) Foreign Application Priority Data

Nov. 29, 2000 (DE) ............................. 100 59 336

(51) Int. Cl.
*C07K 14/51* (2006.01)
*A61K 38/00* (2006.01)
*A61K 35/32* (2006.01)

(52) U.S. Cl. ........................ 514/12; 530/350; 514/2; 514/8

(58) Field of Classification Search ................... None
See application file for complete search history.

(56) References Cited

U.S. PATENT DOCUMENTS

| 5,013,649 | A | | 5/1991 | Rosen et al. |
| 5,264,209 | A | * | 11/1993 | Mikayama et al. ......... 424/85.2 |
| 5,674,844 | A | | 10/1997 | Kuberasampath et al. |
| 5,834,179 | A | * | 11/1998 | Jones et al. .................... 435/4 |
| 6,333,312 | B1 | * | 12/2001 | Kuberasampath et al. .... 514/12 |
| 6,395,883 | B1 | * | 5/2002 | Jones et al. ................. 530/399 |

FOREIGN PATENT DOCUMENTS

| WO | WO 93/05751 | * | 8/1992 |
| WO | WO-97 00886 A | | 1/1997 |
| WO | WO-98/55137 | | 12/1998 |
| WO | WO-00 56879 A | | 9/2000 |

OTHER PUBLICATIONS

Human Bone Morphogenetic protein 2 contains . . . Activity, Ruppert, et al., European Journal of Biochemistry, vol. 237, No. 1. Apr. 1996.

Abstract, Database EPODOC Online, European Patent Office, The Hague,, & CN 1 165 189 A—No. 4 Army Medical School) Nov. 19, 1997.

Advances in refolding of proteins . . . *E. coli*, Lilie, et al. Current Opinion in Biotechnology vol. 9, 1998.

Pro-sequence-assisted protein folding, Eder, et al., Molecular Microbiology, vol. 16. 1995.

Requirement for Activin A and Transforming . . . Assembly, Gray, et al., Science, vol. F247, Mar. 16, 1990.

In Vitro Folding of Inclusion Body Proteins, Rudolph, et al., Faseb Journal, vol. 10, No. 1, 1996.

GDF-8 Propeptide Binds to GDF-8 and Antongizes Biological Activity by Inhibiting GDF-8 Receptor binding, Thies, et al. Genetics Inst. (2000).

The Prodomain of BMP-7 targets the BMP-7 Complex to the Extracellular Matrix, Gregory, et al. The Jour. Of Biol. Chem. (2005).

The Activity and signaling range of mature BMP-4 is regulated by sequential cleavage at two sites within the prodomain of the precursor, Cui, et al. Genes & Del. (2001).

BMP-4 is proteolytically activated by Furin and/or PC6 during vertebrate Embryonic Development, Cui, et al. The EMBO Journ. (1998).

Mutation of an upstream cleavage site in the BMP4 prodomain leads to tissue-specific loss of activity, Goldman, et al. Dept. of Cell & Devl. Biology (1993).

Regulation of Bone Morphogenetic Protein Activity by Pro Domains and Proprotein Convertases, Constam, et al. Harvard Univ. (1999).

Crystal Structure of BMP-9 and Functional Interactions with Pro-region and Receptors, Brown, et al. Struc. Bio. Lab. (2005).

The Pro Domain of Pre-Pro-Transforming growth Factor β1 When Independently Expressed Is a Functional Binding Protein for the Mature Growth Factor, Gentry, et al. Dep. of Biochemistry (1990).

* cited by examiner

*Primary Examiner*—Elizabeth C. Kemmerer
*Assistant Examiner*—Christina Borgeest
(74) *Attorney, Agent, or Firm*—Fulbright & Jaworski LLP (57) ABSTRACT

In order to recombinantly prepare a biologically active protein of the TGF-β superfamily, a protein, whose amino terminus consists of the pro sequence of a protein of the TGF-β superfamily, or parts thereof, to which the mature domain of this protein or of another protein of TGF-β superfamily which exhibits at least 35% homology with mature BMP-2 is attached, is expressed in prokaryotes under conditions in which at least a part of the protein is obtained in the form of inclusion bodies, the inclusion bodies are isolated and solubilized under denaturing conditions, the denatured, monomeric and biologically inactive protein which has been solubilized from the inclusion bodies is renatured, with folding and dimerization to give the soluble, biologically active conformation and, where appropriate, after the renaturation, the mature protein is released proteolytically from its pro form.

4 Claims, 8 Drawing Sheets

Figure 1: SDS-PAGE proBMP-2
1 - LMW
2 - 5 - IB Preparation
6 - Renatured proBMP-2 (n. red)

Figure 2:
Far UV CD spectra of proBMP-2 renatured and denatured

Figure 3:
Emission spectra of proBMP-2, renatured and denatured
($\lambda_{exc}$ = 280 nm; nonidentical protein concentrations)

Figure 4:
SDS-PAGE drBMP-2
1.6-LMW
2-5-drBMP-2, n. red

Figure 5:
RP-HPLC chromatogram drBMP-2

Figure 6:
Far UV CD spectra of drBMP-2 renatured, denatured and reduced

PRODUCTION OF RECOMBINANT BMP-2

The present invention relates to a process for obtaining biologically active drBMP-2 (dr: digit removed), and homologous proteins, by renaturing denatured, biologically inactive proBMP-2 and, where appropriate, subsequently eliminating the propeptide, with the renatured pro form of the protein already being biologically active, to proBMP-2 as a novel product and to its use for producing a composition for promoting bone growth.

BMP-2 belongs to the family of bone morphogenetic proteins (BMPs). These proteins are bone growth factors whose cloning and characterization were achieved for the first time in 1988. The characteristic property of these proteins is the ability to induce endochondral bone neoformation [Wozney et al., Science 242 (1988), 1528-1534].

Structurally, BMP-2 belongs, together with more than 30 other proteins, to the TGF-β superfamily, the members of which exhibit a very high degree of structural similarity to each other although their sequence identity is in some cases less than 30% [Griffith et al., Proc. Natl. Acad. Sci. USA 93 (1996), 878-883]. The essential structural feature of these proteins is what is termed the "cystine knot". This is formed by four antiparallel β-pleated sheet strands, two of which are in each case linked to each other by way of disulfide bonds. In connection with this, two cystines form, together with the peptide backbone, a ring through which a third disulfide bridge extends.

β-Pleated sheets are the dominant secondary structural element in these proteins. However, in these proteins, they are longer and more tightly twisted than in other β-pleated sheet-rich proteins. Because of the structural relatedness of the proteins of the TGF-β family to each other, we have postulated that these proteins also assume their native conformation, that is fold, in a similar manner.

BMPs and related proteins, such as DPP (decapentaplegic, *Drosophila*), play an important role in the embryonic development of higher organisms. Defects in BMP genes or BMP receptor genes, or their regulation, lead to what are in some cases severe developmental disturbances, such as fibrodysplasia ossificans progressiva [Kaplan et al., Calcif. Tissue Int. 47 (1990), 117-125; Rao et al., Hum. Genet. 90 (1992), 299-302; Shafritz et al., N. Engl. J. Med. 335 (1996), 555-561] and dentinogenesis imperfecta [Tabas et al., Clin. Orthop. 293 (1993), 310-316]. Mouse BMP deletion mutants die as early as in the embryonic stage or shortly after birth and exhibit malformations of the skeleton and a very wide variety of organs, such as the heart, kidneys and eyes [Dudley et al., Genes Dev. 9 (1995), 2795-2807; Zhang and Bradley, Development 122 (1996), 2977-2986].

BMPs and similar growth factors are only suitable for treating systemic diseases, such as osteoporosis, under certain circumstances since they can elicit non-tolerable side effects, such as tumor promotion. Rather, BMPs, in particular BMP-2, are particularly suitable for locally restricted applications. These include, inter alia, spinal fusions in connection with degenerative diseases of the vertebral column, the neoformation of cranial bones, maxillofacial surgical interventions and the treatment of complicated fractures of the bones of the extremities. In the case of these applications, the positive effect of rhBMP-2 (rh—recombinant human) on bone neoformation, and consequently on the healing process, has already been impressively demonstrated in several animal models [Lane et al., Clin. Orthop. 361 (1999), 216-227; Marden et al., J. Biomed. Mat. Res. 28 (1994), 1127-1138; Mayer et al., Plast. Recontr. Surg. 98 (1996), 247-259; Sandhu and Boden, Orthop. Clin. North Am. 29 (1998), 621-631; Toriumi et al., Arch. Otolyryngol. Head Neck Surg. 117 (1991), 1101-1112; Yasko et al., J. Bone Joint Surg. (Am.) 74 (1992), 659-670]. In the case of spinal fusion operations, the first clinical studies are even available [Boyne et al., Int. J. Periodontics Restorative Dent. 17 (1997), 11-25; Howell et al., Int. J. Periodontics Restorative Dent 17 (1997), 124-139]. It is likewise appropriate to use rhBMP-2 for fixing artificial joints or screw fittings, as are used, for example, for stabilizing fractures, in the surrounding bone tissue.

Apart from the studies which are still lacking, and also these studies themselves, it is, in particular, the high costs of obtaining the proteins which stand in the way of using BMPs routinely in clinical practice. The process which is described in the present invention enables biologically active BMP-2, as well as related BMPs, to be prepared recombinantly, economically and at high purity, with little technical input and yields which have previously not been thought possible.

Human BMP-2 is synthesized in the body in the form of a preproprotein of 396 amino acids in length. The signal peptide (pre sequence) serves in vivo for transporting the nascent polypeptide chain into the endoplasmatic reticulum (ER). After it has been imported into the ER, the protein folds into its native conformation, the disulfide bridges ($Cys^{296}$-$Cys^{361}$, $Cys^{325}$-$Cys^{393}$, $Cys^{329}$-$Cys^{395}$, intermolecular: $Cys^{360}$-$Cys^{360}$), are formed and posttranslational modifications take place. The latter include the glycosylation of asparagine residues and the, partially incomplete, elimination of the propeptide [Israel et al., Growth Factors 7 (1992), 139-150]. The 114 C-terminal amino acids ($Gln^{283}$-$Arg^{396}$) of the precursor protein form the mature BMP-2, whose biologically active form is a disulfide-bridged ($Cys^{360}$-$Cys^{360}$) homodimer.

Isolating BMP-2 from bone tissue requires substantial input and only results in low yields (40 μg of BMP mixture from 40 kg of bovine bone powder) [Wozney et al., Science 242 (1988), 1528-1534]. Furthermore, isolation from human bone material is ethically dubious and involves the danger of contamination with pathogens (prions, HCV, etc.). The use of homologous proteins from pigs or cattle is likewise risky from the immunological point of view.

Preference is therefore given to preparing BMP-2 recombinantly. There are two primary possibilities for doing this. In the first place, the protein can be obtained in eukaryotic expression systems [Wang et al., Proc. Natl. Acad. Sci. USA 87 (1990), 2220-2224]. Disadvantages of this approach are the relatively low quantities of recombinant protein (25 μg of partly purified BMP-2 per 1 l of medium [Wozney et al., Science 242 (1988), 1528-1534]) and the relatively high degree of technical input and the costs resulting from this.

The second route involves using prokaryotic expression systems. Their advantages lie in simple technical manipulation, low costs and the isolation of very high quantities of protein. However, in contrast to eukaryotes, bacteria are unable to process the precursor protein correctly. For this reason, the method which has thus far been used is restricted to expressing the mature domain of BMP-2 ($Gln^{283}$-$Arg^{396}$). In bacteria, this domain accrues in an insoluble, biologically inactive form since, as a result of the reducing conditions in the cytosol, inter alia, it is not possible for the disulfide bridges of the protein to be formed. These insoluble protein aggregates are termed inclusion bodies (IBs), whose isolation and purification has been described, for example, by Marston [Biochem. J. 240 (1986), 1-12].

The method of Ruppert et al., [Eur. J. Biochem. 237 (1996), 295-302] for renaturing mature BMP-2 is based on U.S. Pat. No. 5,650,494 [Cerletti et al., 1997], which relates to TGF-β-like proteins, which also include BMP-2. The method involves renaturing the monomeric, denatured mature form of TGF-β-like proteins in the presence of a mild detergent, to give the biologically active conformation. In the case of BMP-2, this only resulted in yields of 0.2 mg of active protein per 1 g of cells being obtained [Ruppert et al., Eur. J. Biochem. 237 (1996), 295-302].

However, using the present invention, it is possible to obtain a yield of active protein which is more than 25 times as high, based on the induced cell mass. Indeed, the yield is about three orders of size higher than that achieved when expressing in eukaryotic cells.

Because of the complicated disulfide pattern (cystine knot), the yields are very low when renaturing mature BMPs which are expressed recombinantly in *E. coli*. The present invention is based on the hypothesis that the BMP-2 propeptide, like the propeptides of homologous proteins as well, is partly responsible for the correct folding of the mature domain.

The process according to the invention for recombinantly preparing a biologically active protein of the TGF-β superfamily is characterized in that (a) a protein, whose aminoterminus consists of the pro sequence of a protein of the TGF-β superfamily, or parts thereof, to which the mature domain of this protein, or of another protein of the TGF-β superfamily which exhibits at least 35% homology with mature BMP-2, is attached, is expressed in prokaryotes under conditions in which at least a part of the protein is obtained in the form of inclusion bodies, (b) the inclusion bodies are isolated and solubilized under denaturing conditions, (c) the denatured, monomeric and biologically inactive protein, which has been solubilized from the inclusion bodies, is renatured, thereby enabling folding and dimerization to give the soluble, biologically active conformation, and (d) where appropriate, after the renaturation, the mature protein is proteolytically released from its pro form.

Our in vitro renaturation experiments have shown that it is possible according to the invention, even in the absence of detergents, to obtain large quantities of biologically active drBMP-2 relatively simply by using the hypothetical pro form of BMP-2 ($Gly^{20}$-$Arg^{396}$) and then eliminating the propeptide ($Gly^{20}$-$Arg^{282}$). In this connection, drBMP-2 is to be understood as meaning the C-terminal domain of BMP-2 from $Lys^{290}$, $Arg^{291}$ or $Leu^{292}$ (see example 2.2.1) to $Arg^{396}$, the biological activity of which has been described by Koenig et al., [Mol. Cell Biol. 14 (1994), 5961-5974]. The amino acids ($Gln^{283}$ to $Arg^{289}$, Lys290 or $Arg^{291}$) mediate the binding of BMP-2 to heparin.

While this interaction, which is, if anything, nonspecific, modulates the effect of BMP-2, it is not essential for the biological activity of the latter [Ruppert et al., Eur. J. Biochem. 237 (1996), 295-302].

According to the invention, either the entire pro sequence ($Gly^{20}$-$Arg^{282}$) or a part of it can be used as the pro sequence or propeptide.

In order to increase the rate of expression of probmp-2 in prokaryotes, it is possible, according to the invention, to attach a tag sequence, e.g. a histidine tag, to the 5' end of the sequence encoding this gene, or to use mutagenesis to optimize the probmp-2 codons for prokaryotic expression. It is also possible to augment expression as described in U.S. Pat. No. 5,336,602 [Brinkmann et al., 1993] or to use a combination of these methods.

When recombinant probmp-2 is overexpressed in the cytoplasm of prokaryotes, the protein then accrues in the cytoplasm in the form of inactive, insoluble aggregates (inclusion bodies—IBs). In order to isolate them, the cells are first of all disrupted, after fermentation, by means of one or more of the customary methods (e.g.: high pressure dispersion, enzymic lysis or ultrasonication), with this preferably taking place in a neutral to weak acid buffer solution, for example 0.1 M tris/HCl pH 7.0.

The cellular DNA is degraded, by means of mechanical, chemical or, preferably, enzymic treatment, into fragments which do not cosediment with the IBs. Insoluble cell constituents, including the IBs, are then separated off from the soluble constituents in any appropriate manner, with separation by centrifugation being preferred. The pellet is washed with solutions which, as a result of their composition or of substances added to them, such as detergents, are able to solubilize interfering cell proteins and membrane components, but not the recombinant proBMP-2, from the IBs. The remaining, insoluble, proBMP-2-containing fraction is then subsequently solubilized, renatured and enzymically processed in accordance with the invention.

Prior to the renaturation, the IBs are solubilized, with use being made of customary denaturing agents (chaotropic substances) or combinations of these agents. These agents include, inter alia, guanidinium salts, e.g. GdmCl or GdmSCN, and also urea and its derivatives. In this connection, the concentration of the denaturing agent or denaturing mixture is to be adjusted such that the recombinant, difficulty soluble protein can be completely solubilized. In the case of guanidinium chloride, these concentrations lie in the range of 3-8 M and, in the case of urea, of 6-10 M. In order to monomerize the soluble, cystine-containing protein, which has thus been denatured, completely as well, preference is given to adding a reducing agent, such as dithiothreitol (DTT) or β-mercaptoethanol, or a combination of reducing agents, with the pH of the solubilization buffer preferably being adjusted to between 8 and 9. Following the solubilization, or in parallel with it, it is also possible to covalently modify the free cysteines, for example using oxidized glutathione. After the solubilization, or the optional covalent modification of the cysteines, the pH of the IB solubilizate is preferably adjusted to 5 or less and, once again optionally, excess redox equivalents are removed by dialysis, with the dialysis buffer, apart from the reducing agent, expediently having the same composition as the solubilization buffer. Finally, the constituents which remain insoluble during the solubilization process are separated off (centrifugation or filtration) and discarded. The optional modification step, and the removal of the excess reducing agent, enable the IB solubilizate to be prepurified, where appropriate, by means of immobilized metal affinity chromatography (IMAC) provided the proBMP-2 was expressed with an N-terminal histidine tag.

The process according to the invention for renaturing rh-proBMP-2 involves decreasing the concentration of the denaturing agent(s) down to a level (e.g. $\leq 0.5$ M GdmCl) which does not have a denaturing effect or only has a weakly denaturing effect. This is preferably effected by slowly diluting the solubilizate, continuously or stepwise, in renaturation buffer. In order to maximize the yield of biologically active protein, care must be taken to ensure that the intermixing in this connection takes place as speedily and thoroughly as possible, something which is ensured, for example, by vigorous stirring.

An alternative to dilution is that of dialyzing the solubilizate against renaturation buffer. The conditions are in each case to be selected such that the formation of protein aggregates is minimal. Renaturation of the protein may already take place during the initial dilution of the denaturing agent. After dilution or dialysis, the final concentration of rh-proBMP-2 in the renaturation buffer is 10-1 000 μg/ml, preferably 50-250 μg/ml.

Optimal protein concentration is ensured when the unproductive aggregation of incorrectly folded polypeptide chains and folding intermediates (a $\geq$2nd order process [Kiefhaber et al., Biotechnology (N.Y.) 9 (1991), 825-829]) proceeds significantly more slowly than does the folding of the individual polypeptide chains to give the native conformation (1st order process).

The pH of the renaturation buffer employed is 6.5-10, ideally 8-9. Suitable buffers are consequently any buffers which have a neutral to alkaline $pK_a$, preferably tris buffers and phosphate buffers and combinations of these buffers. It is furthermore expedient to add low molecular weight auxiliary agents which increase the renaturation yield [U.S. Pat. No. 5,593,865, Rudolph et al., 1955] to the renaturation buffer. It is particularly suitable to renature in the presence of L-arginine, with use being made of concentrations of 0.2-2.0 M, preferably 0.5-1.5 M, L-arginine. Another component of the renaturation buffer is, according to the invention, a combination of the reduced and oxidized forms of one or more thiol compounds. Examples of such combinations are reduced (GSH) and oxidized (GSSG) glutathione, cysteine and cystine, cysteamine and cystamine, and also β-mercaptoethanol and 2,2'-hydroxyethyl disulfide. An artificial redox system of this nature can be used to control the renaturation of the protein thermodynamically. The possibility of forming the disulfide bridges, which is necessary for the correct folding of the polypeptide chains [Creighton, Biochemistry 378 (1997), 731-744], is ensured by the presence of the oxidized form, while the possibility of rebreaking incorrectly formed cystines (reshuffling) is ensured by the presence of the reduced form of the thiol component [Creighton et al., Trends Biotechnol. 13 (1995), 18-23].

Preference is given to using glutathione in reduced (GSH) and oxidized (GSSG) form at concentrations of in each case up to 10 mM, ideally in a ratio of 5 mM GSSG to 2 mM GSH.

According to the invention, the renaturation buffer preferably contains one or more chelating agents, such as EDTA (ethylenediaminetetraacetic acid), at concentrations of up to 20 mM (preferably approx. 5 mM) in order, on the one hand, to prevent the uncontrolled, accelerated oxidation of the reduced thiol component by metal ions and, on the other hand, to inhibit metalloproteases which might contaminate the renaturate.

According to the invention, the renaturation is expediently effected at temperatures of 0-20° C. over 1-21 d, preferably 5-10° C. and 5-10 d.

The relatively long renaturation times can be explained by the covalent dimerization of the proBMP-2 polypeptide chains. Our experiments have shown that, under the conditions of the present invention, it is the oxidation of free thiol groups, and not the protein concentration, which determines the rate of this process.

After the renaturation process has been concluded, the renaturation mixture is, according to the invention, dialyzed against a preferably acid (pH$\leq$5) buffer which does not contain any low molecular weight auxiliary agents within the meaning of the present invention. In this connection, the dialysis buffer conforms to the process according to the invention when the dialysis, to the greatest possible extent, aggregates incorrectly folded polypeptide chains and folding intermediates, which can consequently be separated off by means of centrifugation, filtration or another customary method. Prior to the dialysis, it is expedient to concentrate the renaturation mixture, for example by means of cross-flow filtration, which can be followed by an additional incubation time under renaturation conditions. Aerating the buffer, something which may also possibly take place in association with the process of concentrating, and which accelerates the oxidation of free thiol groups, may have the effect of shortening the renaturation time. This can also be achieved by adding substances which have an oxidizing effect.

According to the invention, chromatographic separating methods can be used to separate monomeric, incorrectly folded or non-dimerized, correctly folded species from the native, dimeric form of the renatured rh-proBMP-2, with preference being given to using reversed-phase HPLC. Suitable column materials for this purpose, are, in particular, silica-based C4-matrices or polymer-based particles of comparable or stronger hydrophobicity, with a pore diameter of $\geq$300 Å being advisable due to the size of the protein. Suitable eluents are those which are customary in RP-HPLC, such as acetonitrile, 2-propanol or ethanol. According to the invention, use is made, in this connection, of ion-pair formers, preferably trifluoroacetic acid or perfluorobutyric acid, at the customary concentrations.

Another possibility for purifying dimeric, naively folded proBMP-2 is that of using heparin affinity chromatography. In this connection, urea concentrations of from 2 to 8 mol/l, preferably 5 mol/l, should be used as an addition to the buffer in order to increase the solubility of the protein and avoid nonspecific interactions between proBMP-2 and the column material. HiTrap Heparin-Sepharose (Amersham Pharmacia Biotech) is a particularly suitable column material in this context. The monomeric forms of proBMP-2 are then eluted from the matrix at less than 300 mol of NaCl/l while the dimeric form is eluted at higher salt concentrations.

WO 00/22119 [Rattenholl et al., 2000] has already described a method for isolating the biologically active protein from its inactive, denatured pro form in the case of the nerve growth factor β-NGF, which does not belong to the TGF-β family. β-NGF and BMP-2 differ, in particular, in the length of their pro sequence (β-NGF-103 AA; BMP-2-263 AA). There are also significant differences in the tertiary structure [McDonald and Hendrickson, Cell 73 (1993), 421-424]. It is not surprising, therefore, that the present invention differs from WO 00/22119 in essential points.

The renaturation times which are required for maximal yields of correctly folded rh-proBMP-2 are significantly longer (1-21 d) than are those for rh-proNGF (3 h). In vivo, the pro form of BMP-2, like that of β-NGF, is processed by prohormone convertases of the furin type. These convertases recognize a dibasic sequence motif at the end of the pro sequence. Their last amino acid is $Arg^{282}$. In vitro, proteases having comparable substrate specificity are able to eliminate the BMP-2 propeptide or β-NGF propeptide.

However, the processing of the renatured rh-proBMP-2 requires entirely different conditions from those employed for cleaving proNGF. Although the BMP-2 pro sequence which is used in accordance with the invention is, with 263 AA, substantially longer than the mature protein (114 AA), it has surprisingly been found, in our experiments, that the solubility properties of proBMP-2 are determined by its mature domain. In contrast to the BMP-2 propeptide on its own ($Gly^{20}$-$Arg^{282}$), proBMP-2 is therefore only soluble at high concentrations, without any solubilizing additives, at a pH of $\leq$5. At acid pH, it is not possible to use proteases (trypsin, PACE (paired basic amino acid-converting enzymes; eukaryotic endopeptidases which cut after dibasic motifs)) to efficiently process the pro form. However, in order to enable proteolytic cleavage to take place, use is made, according to the invention, of any noninhibiting solubilizers, in particular urea or trishydroxymethylaminomethane (tris) at concentrations of 1-5 M and 0.1-2 M, respectively, either individually or in combination, preferably 2-4 M urea in combination with 0.1-1 M tris. Using these additives, it is possible to keep proBMP-2 in solution at concentrations of ≧1 mg/ml even at the pH optimum (7-8) of the proteases employed.

Dialysis is expediently used to adjust the buffering conditions for the proteolysis. According to the invention, preference is given to trypsin-like proteases, which are used in a mass ratio of from 1:10 to 1:1 000 (trypsin, rh-proBMP-2), preferably of from 1:20 to 1:100. The mixture is incubated over a period of from 1 min to 24 h, preferably of from 30 min to 6 h, at a temperature of 0-37° C., preferably 10-25° C. In the case of tris, the solubilizer itself functions as the buffering substance while, in the case of urea, tris buffer, which is added in addition at the given concentrations, functions as the buffering substance. Furthermore, a high concentration of tris, e.g. 0.5 M, prevents the covalent modification of amino acid side chains by isocyanate which may have been formed from the urea.

The pH is adjusted to a value which is favorable for the protease concerned, preferably 7-8. In order to suppress nonspecific proteolytic degradation by metalloproteases, it is expedient, according to the invention, to add chelating agents, e.g. 1-20 mM EDTA. The proteolysis is stopped by adding one or more protease inhibitors, preferably 1-5 mM phenylmethylsulfonyl fluoride (PMSF) or trypsin inhibitor obtained from bovine pancreas or soybeans (BPTI/SBTI) in a 2-20-fold molar excess relative to the trypsin, or by using acid to adjust the pH to ≦5 [Rudolph et al.; Folding proteins, in Protein Function: A Practical Approach, T. E. Creighton (Ed.), 2nd Edtn. (1997), 57-99].

The N-terminus of the mature BMP-2 ($Gln^{283}$-$Arg^{291}$) is unstructured and therefore protease-sensitive. In addition, it contains some arginine and lysine residues ($Arg^{289,291}$, $LyS^{285, 287, 290}$) The limited proteolysis with trypsin, which preferably cuts after these basic amino acid residues, therefore also leads to the flexible N-terminus of mature BMP-2 being eliminated. The biological activity of the resulting drBMP-2 has been demonstrated in animal experiments. According to the invention, it is possible, where appropriate by means of protein engineering, to introduce an additional disulfide bridge for the purpose of fixing and stabilizing the mature BMP-2 N-terminus, e.g. as is present in the related TGF-β, in order, in this way, to protect the BMP-2 heparin-binding site from proteolytic degradation. Our experiments on the limited proteolysis of rh-proBMP-2 in the absence of solubilizer concentrations according to the invention, at protein concentrations which are then correspondingly low, have shown that the propeptide consists of at least one domain which is still largely protease-resistant following elimination from the mature protein. Some of the solubilizers which are used themselves have a weakly denaturing effect at the concentrations employed. This results in the BMP-2 propeptide, which is not stabilized by intracatenary disulfide bridges, being structurally destabilized and protease-labile and consequently being able to be degraded under the conditions of limited proteolysis according to the invention.

Because of the extreme hydrophobicity of native BMP-2 [Scheufler et al., J. Mol. Biol. 287 (1999), 103-115], purification by way of hydrophobic interactions suggests itself as a method for purifying the proteolysis products. According to the invention, preference is given to using, for this purpose, column materials to which the drBMP-2 which has been obtained binds strongly, whereas the other degradation products, and the protease employed and/or the inhibitor, only interact weakly with the material. In conformity with the present invention, it is possible to alter the buffering conditions after the proteolysis such that the drBMP-2 precipitates while the other degradation products, the protease and/or its inhibitor(s) remain in solution. After it has been separated from the supernatant, the precipitated drBMP-2 can then be solubilized once again in suitable buffers or solvents. This change to precipitating conditions in the presence of a suitable column material, in particular "Fractogel EMD Phenyl S" (Merck) or comparable materials, such as Phenylsepharose (Pharmacia), is preferably effected by means of dialysis. If the material is used in a large excess, it is possible to achieve the situation where the protein binds to this material before it aggregates. After the column material has been loaded with protein in this way, the unwanted components can be removed by means of suitable washing steps. The drBMP-2 is expediently eluted under conditions which are mildly to strongly denaturing but in no way reducing. Depending on the column material, suitable eluents are accordingly, inter alia, arginine, urea or guanidinium salts which, in low concentrations, can also be used for washing the column material. After the elution, the drBMP-2-containing fractions are, where appropriate, combined and, particularly preferably, dialyzed against 0.1% trifluoroacetic acid (TFA) or ammonium acetate, which are very suitable solvents for the final application of BMP-2. According to the invention, it is also possible to separate the proteolysis products using reversed-phase materials, preferably $C_4$-RP-HPLC, with the elution preferably being carried out using 0.1% TFA in an acetonitrile gradient.

Mature BMP-2, which is renatured in accordance with the invention and obtained after eliminating the pro sequence, can be used, in the manner which is customary for this purpose, for promoting bone growth. Surprisingly, however, the renatured proBMP-2 itself, which still contains the entire pro sequence or a truncated pro sequence, is also equivalent to the mature BMP-2 in its biological activity and can be used like the mature BMP-2. Part of the subject matter of the invention is therefore also a pharmaceutical for promoting bone growth which comprises proBMP-2 as the active compound. The proBMP-2 can contain the complete pro sequence or a truncated pro sequence. Preference is given, according to the invention, to using a combination of proBMP-2 and various medical implant materials for both temporary bone replacement (bone replacement materials) and permanent bone and joint replacement (metal implants such as hip and knee joint endoprostheses) in traumatology, orthopedics, ear, nose and throat surgery, oral and maxillofacial surgery and neurosurgery. In this connection, proBMP-2 can, in the first place, be used as an additional implant coating in the nature of a thin protein film which adheres, with or without adhesives (e.g. silane), to all the inner and outer surfaces. In the second place, proBMP-2 can be used as an integral constituent of implants by adding it to the nonsolid precursors of those solid end products which can be prepared by chemical polymerization or curing (e.g. calcium phosphate cements such as Norian SRS, Ostim, and others).

Inorganic and organic materials of natural or artificial origin, and also mixed forms of these two materials, are suitable for use as implants for transient bone replacement. Examples of inorganic bone replacement materials are ceramic materials composed of hydroxyapatite, beta-tricalcium phosphate, alpha-tricalcium phosphate, glass ceramic materials, bioglasses, calcium carbonates, calcium sulfates and other (not listed) calcium salts in crystalline and amorphous form, including injectable calcium phosphate-based bone cements. Suitable organic materials are, inter alia, collagens, bone tissue, demineralized bone matrix, gellable polysaccharides such as hyaluronic acid, biocompatible synthetic materials, such as polylactic acid, polymethyl acrylates, polyethylene glycols, and others, in the widest possible variety of mixed forms and processing forms. Endoprostheses and other metal implants, such as those for vertebral stabilization, are suitable for permanent bone replacement. These latter are customarily products composed of different stainless steels and titanium alloys, some of which are also provided with hydroxyapatite coatings.

Other parts of the subject matter of the invention are therefore proBMP-2 possessing the complete or truncated pro sequence to which the mature BMP-2 is bonded, a pharmaceutical comprising this substance and a process for producing a pharmaceutical for promoting bone growth as defined in the patent claims. The complete sequence of proBMP-2 from $Gly^{20}$-$Arg^{396}$, including 20 amino acids of His tag and the start codon Met, is shown in table 2. The amino acids Met1 to His20 are a constituent of the pET-15b-encoded His tag. The pro sequence of BMP-2 begins at $Gly^{22}$. The additional methionine is located between the His tag and the pro sequence. $Gly^{22}$ to $Arg^{398}$ in the sequence depicted here correspond to $Gly^{20}$ to $Arg^{396}$ in the primary translation product of the human preproBMP-2 cDNA, to which the sequence data in the text refer.

The following examples explain the invention in combination with the drawing. In this drawing.

EXAMPLES

Implementation Example 1

Preparing proBMP-2

Cloning the probmp-2 cDNA into an *Escherichia coli* Expression Vector

The T7 expression system supplied by Novagen [Studier and Moffat, J. Mol. Biol. 189 (1996), 113-130] was used for cloning the probmp-2 cDNA.

The pcDNA3 vector (Boehringer-Mannheim GmbH) containing inserted preprobmp-2 cDNA was used as the starting DNA.

The DNA encoding amino acids $Gly^{20}$ to $Arg^{396}$ of BMP-2 was obtained by polymerase chain reaction (PCR). In this reaction, use was of mutagenesis primers to insert a methionine codon, for the translation start, at the 5' end, to convert the stop codon at the 3' end into an *E. coli*-typical stop codon and to supplement it with a second stop codon. In addition, the primers respectively contained an NdeI cleavage site (5' end) and a BamHI cleavage site (3' end). This enabled the subsequent cloning into the expression vector pET-15b (Novagen) to take place. This vector additionally encodes an N-terminal 6-histidine tag which enabled the expression rates in *E. coli* to be substantially increased.

After the conclusion of the cloning, the nucleotide sequence was checked by DNA sequencing [Sanger et al., Proc. Natl. Acad. Sci. USA 74 (1977), 5463-5467].

The following primers were used:

```
forward primer "PrimerFwProBMP":
                NdeI
5'-cg gaa ttc   ca|t atg ggt gcg gct ggc ctc gtt cc-3'
                     Met Gly Ala Ala Gly Leu Val
                     H2N → reverse primer "PrimerRevBMP":
              BamHI
5'-cc   g|ga tcc tta cta gcg aca ccc aca acc-3'
                    Stp Stp Arg Cys Gly Cys Gly
                                            HOOC←
```

*E. coli* BL21 (DE3) was used as the host strain. The chromosome in these bacteria contains the gene for T7-RNA-Polymerase, which is under the control of the lac promoter. Expression of the polymerase can therefore be induced with isopropyl-β-D-thiogalactoside (IPTG). The probmp-2 gene is controlled by a T7 promoter. Induction with IPTG consequently leads to the formation of proBMP-2. In order to further increase the expression rate, the cells were cotransformed with pUBS520. This plasmid contains the gene for an arginine tRNA (dnay) which is rare in *E. coli*. On the other hand, the arginine codons (AGA and AGG) which this tRNA recognizes occur particularly frequently in eukaryotic genes and therefore also in probmp-2. The expression rate of these genes in *E. coli* depends, inter alia, on the availability of this tRNA [Brinkmann et al., Gene 85 (1989), 109-114].

Expressing Human proBMP-2 in *E. coli*

In order to propagate the recombinant bacterial strain, 100 μg of ampicillin/ml and 50 μg of kanamycin/ml were added to a suitable volume, as a rule 1.5 l, of 2·YT medium, which was inoculated with a single colony.

2·YT Medium (1 l):

17 g of tryptone 10 g of yeast extract 5 g of NaCl

The culture was shaken at 160-200 rpm and 37° C. The culture was induced with 1 mM IPTG at an $OD_{600}$ of 1-1.3. The culture was then shaken at the same temperature for a further 3-4 h and, in this way, reproducible cell densities following induction of $OD_{600}$ 3-3.5 were achieved. The cells were harvested by centrifuging at 10 000 g. In this way, it was possible to obtain 3-3.5 g of cells (wet weight) per 1 l of medium. As an alternative to immediate cell disruption, the cells were first of all frozen in liquid nitrogen and, after that, at −20° C.

Isolating the Inclusion Bodies (IBs)

When recombinant probmp-2 is expressed, aggregates, i.e. inclusion bodies (IBs), form in the bacteria cells. These IBs were prepared as described in Rudolph et al.: "Folding proteins", in "Protein Function: A Practical Approach", T. E. Creighton (Ed.), 2nd Edtn. (1997), 57-99.

In each case 5 g of cell pellet were resuspended in 25 ml of 100 mM tris/HCl pH 7.0, 1 mM EDTA. After 1.5 mg of lysozyme had been added per 1 g of wet cell weight, the cell suspension was then incubated for 30 minutes at 4° C. Finally, the cells were disrupted by means of high pressure dispersion (Gaulin homogenizer). After 3 mM $MgCl_2$ and 10 μg of DNase/ml had been added, the homogenate was incubated for a further 30 min at 25° C. 0.5 part by volume of 60 mM EDTA, 6% Triton X-100, 1.5 M NaCl, pH 7.0, were then added and the incubation was continued at 4° C. for 30 min in order to solubilize insoluble cell constituents. Under these conditions, the IBs remained insoluble and could be separated off by centrifuging at 39 000 g. In order to remove excess detergent from the IBs again, the latter were washed a further 5 times with 100 mM tris/HCl, pH 7.0, 20 mM EDTA and finally aliquoted and stored at −20° C.

In this way, it was possible to reproducibly obtain 180-210 mg of IBs, which, at a protein content of 30-35%, contained 90-95% rh-pro-BMP-2, from 1 g of induced *E. coli* cells.

Solubilizing the IBs 100-150 mg of IB pellet were solubilized, at 25° C. for 4 h, in 1 ml of 100 mM tris/HCl, pH 8.0, 6 M GdmCl, 100 mM DTT, 1 mM EDTA. After that, the pH was adjusted to 3-4 with acetic acid and the insoluble constituents were pelleted at 16 000 g for 20 min in a centrifuge. The supernatant was then centrifuged once again for 30 min in an ultracentrifuge at 266 000 g in order to separate off microaggregates. The protein concentration was determined by measuring absorption at λ=280 nm [Gill and von Hippel, Anal. Biochem. 182 (1989), 319-326] and was 30-52 mg/ml.

Purifying proBMP-2

Recovery rate (approx. 70%) in this connection was comparable with the analytical scale.

Heparin affinity chromatography on a 1 ml HiTrap Heparin Sepharose (Amersham Pharmacia Biotech) was used as a second purification method. The buffer system employed was:

0.1 mol $l^{-1}$ tris, pH 7.56, 6 mol $l^{-1}$ urea (buffer A), and
0.1 mol $l^{1-1}$ tris/HCl, pH 7.5, 6 mol $l^{-1}$ urea, 1 mol $l^{-1}$ NaCl (buffer B).

The column was equilibrated with more than 10 column volumes of buffer A. Impurities were eluted using a gradient of from 0 to 20% buffer B. Monomeric and dimeric proBMP-2 were separated using a gradient of from 20 to 50% buffer B in 30 min at a flow rate of 1 ml $min^{-1}$.

Renaturing rh-proBMP-2 on a Preparative Scale

The proBMP-2 IB solubilizate, containing 4 M GdmCl, pH 4, was diluted for the renaturation such that, after complete dilution of the solubilizate in folding buffer, the final concentration of GdmCl reached 50-60 mM. The final concentration of proBMP-2 was 3-4 μm (corresponds to 135-180 μg/ml).

Folding Buffer:
100 mM tris/HCl, pH 8.0
1 M L-arginine
5 mM GSSG
2 mM GSH
5 mM EDTA After the folding buffer had been filtered and degassed, the solubilizate was slowly added (~20 ml/h), while stirring, and the mixture was incubated at 5° C. for 7 d. In this connection, the. DTT residues which were entrained with the solubilizate are equivalent to a concentration of at most 0.4 mM GSH.

The folding mixture was concentrated by means of cross-flow filtration (Filtron Minisette, membrane: 30 kDa open channel). The concentrate was then dialyzed five times against 20 volumes of 50 mM Na acetate, pH 5.0, for in each case 24 h and, after that, aggregated protein was centrifuged off at 75 000 g for 2 h. The quantity of protein remaining in solution was determined by absorption at λλ32 280 nm and was reproducibly approx. 50% based on the protein content of the initially employed IB solubilizate.

Purifying proBMP-2

Figure 8:
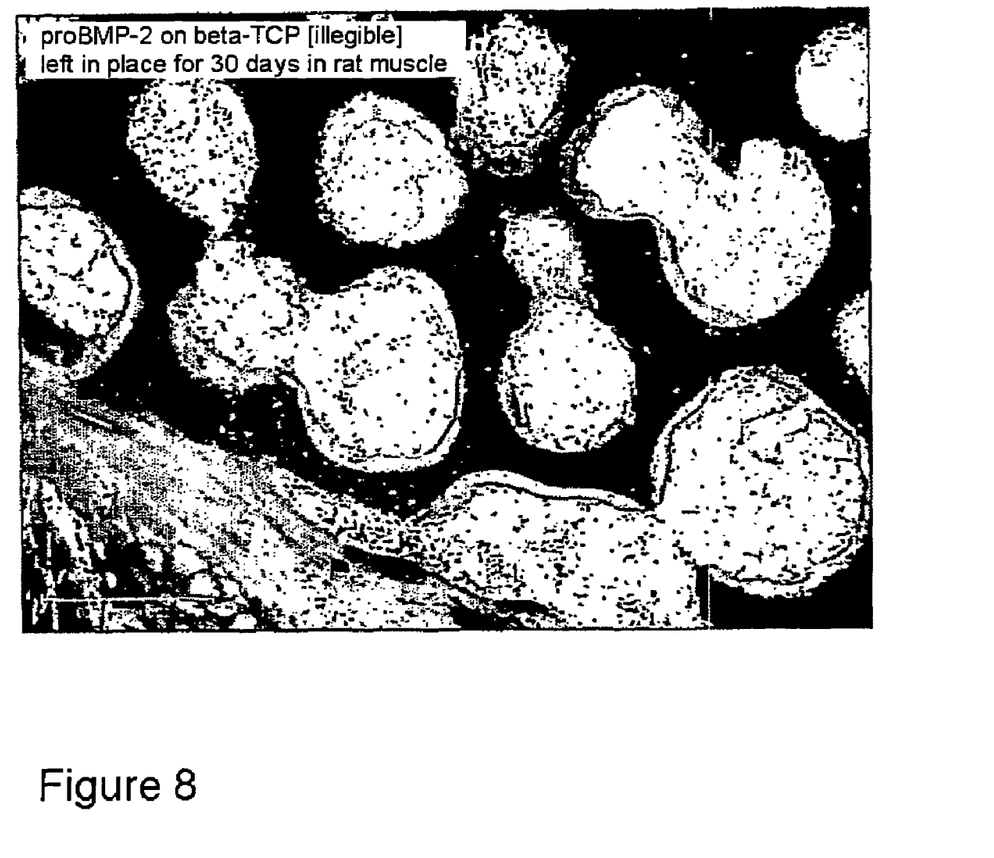
FIG. 8 depicts a histological section of an rh-proBMP-2 implant. Both the inner and the outer surface of the ceramic are coated with bone substance. The interior of the pore contains bone marrow containing numerous fat cells (implant material—dark, bone—light blue). Some muscle fibers (dark blue) and connective tissue can be seen at the bottom left.

RP-HPLC was employed for the analytical or semi-preparative separation of the (incorrectly or correctly folded) monomeric species from native, dimeric rh-proBMP-2. On the analytical scale, use was made, inter alia, of a protein RP column (150×3.6 mm, YMC) using 0.1% perfluorobutyric acid (HFBA) in $H_2O$ or ACN as the mobile phase (see FIG. 8). Separation of monomer and dimer was also achieved using trifluoroacetic acid as ion-pair former. Because of its higher hydrophobicity, the dimer, as in the case of mature BMP-2, elutes at a later stage than does the monomer or the monomeric, incorrectly folded species. On the semipreparative scale, use was made of a column containing Source 15 RPC material (Pharmacia). In this connection, the separation profile and the recovery rate (approx. 70%) were comparable with the analytical scale.

Characterizing rh-proBMP-2

Figure 1:
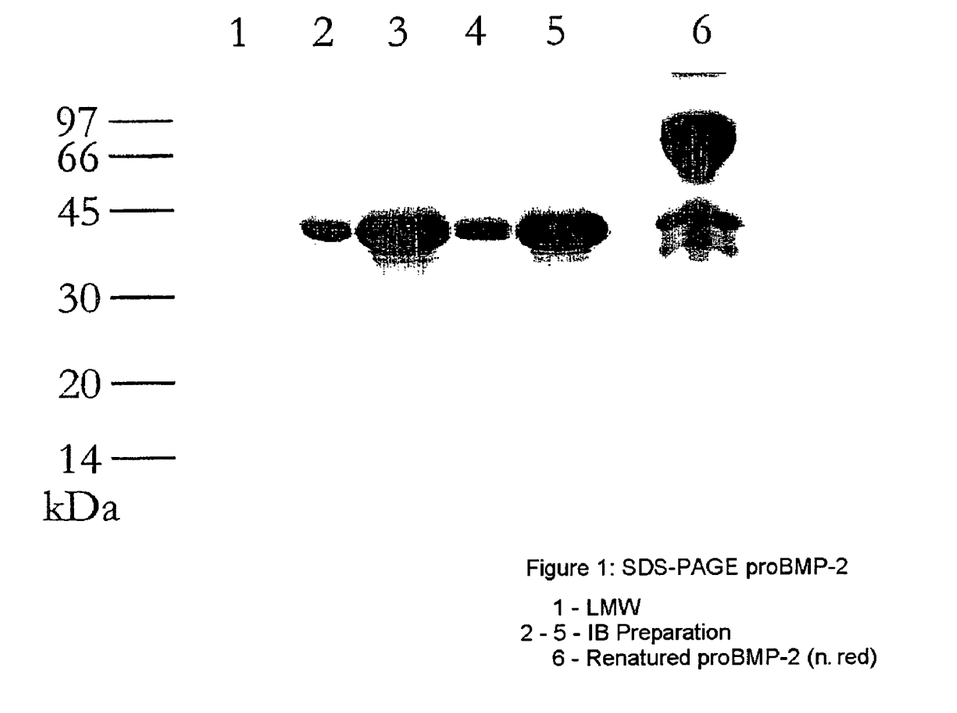
FIG. 1 depicts an SDS-PAGE electropherogram

Purity Analysis and Molecular Weight Determination by Means of SDS-polyacrylamide Gel Electrophoresis The SDS-PAGE analysis indicated that the proBMP-2 IBs which had been prepared in accordance with the invention were highly pure (≧90%; FIG. 1, lanes 2-5), which meant that it was possible to use them for the renaturation without any prior purification.

SDS-PAGE carried out under nonreducing conditions (addition of iodoacetamide leads to irreversible, oxidative modification of free thiol groups) shows that renatured proBMP-2 exhibits a high degree of covalent dimerization (≧90%), with this indicating that the disulfide bridges have been correctly formed and that the protein possesses the native structure (FIG. 1, lane 6).

N-terminal Sequence Analysis

The N-terminal sequencing [Edman and Begg, Eur. J. Biochem. 1 (1967), 80-91] was carried out after performing SDS-PAGE and Western blotting onto a PVDF membrane. In the case of renatured proBMP-2, the sequencing gave the following amino acid sequence:

Gly-Ser-Ser-His-His-

This corresponds to the N-terminus of recombinant proBMP-2 possessing a histidine tag, after the starting methionine has been eliminated.

Circular Dichroism Spectrometry and Fluorescence Spectroscopy

Figure 2:
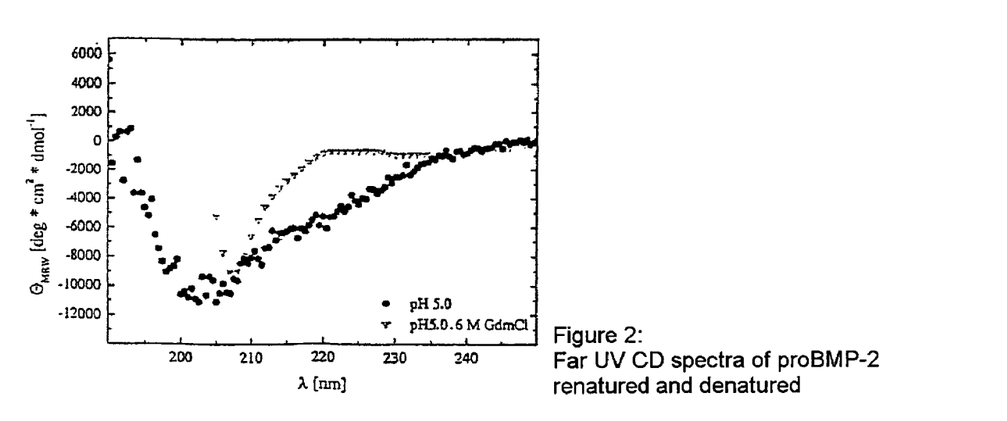
FIG. 2 depicts UV-CD spectra
Figure 3:
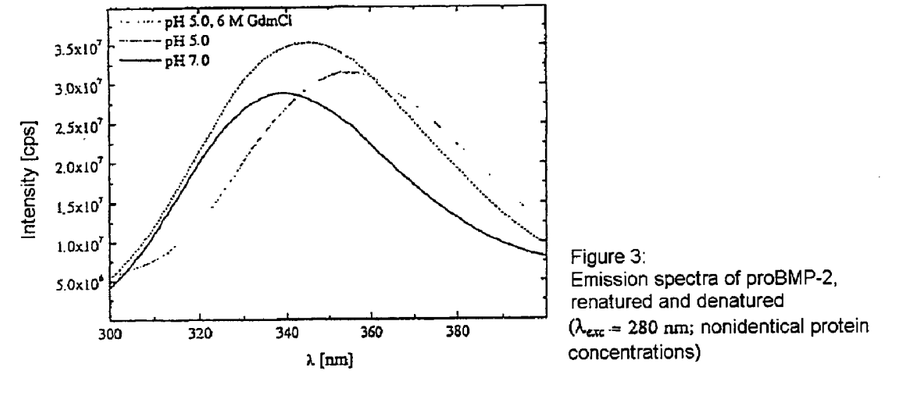
FIG. 3 depicts emission spectra, in each case of proBMP-2

The fluorescence-spectrometric and CD-spectrometric analyses which were carried out on renatured proBMP-2 and on proBMP-2 which had once again been denatured provide clear indications of the presence of secondary and tertiary structure. The marked difference between the ellipticity of renatured and denatured proBMP-2 in the region around λ=220 nm of the far UV CD spectrum (FIG. 2) makes it possible to conclude that secondary structure elements are formed in the renaturation process according to the invention. The shifting of the emission maximum of the fluorescence of renatured proBMP-2 toward lower wavelengths as compared with the denatured protein (FIG. 3) is typical for the formation of native tertiary structures. In this connection, the tryptophan residues of the protein (5 tryptophans per proBMP-2 polypeptide chain) pass from the polar environment of the solvent into the apolar core of the folding protein, where they are also sterically fixed. The excitation energy loss which has been reduced in this way results in light of higher frequency being emitted. [Schmid: "Optical spectroscopy to characterize protein conformation and conformational changes." in "Protein Structure: A Practical Approach", T. E. Creighton (Ed.), 2nd Edtn. (1996), pp. 261-297]. It is also clear from the fluorescence spectra that the structure of proBMP-2 undergoes a change at low pH, that is in the region where mature BMP-2 and proBMP-2 are highly soluble. As our experiments have indicated, this may be attributed to the propeptide unfolding in part (data not shown).

Figure 7:
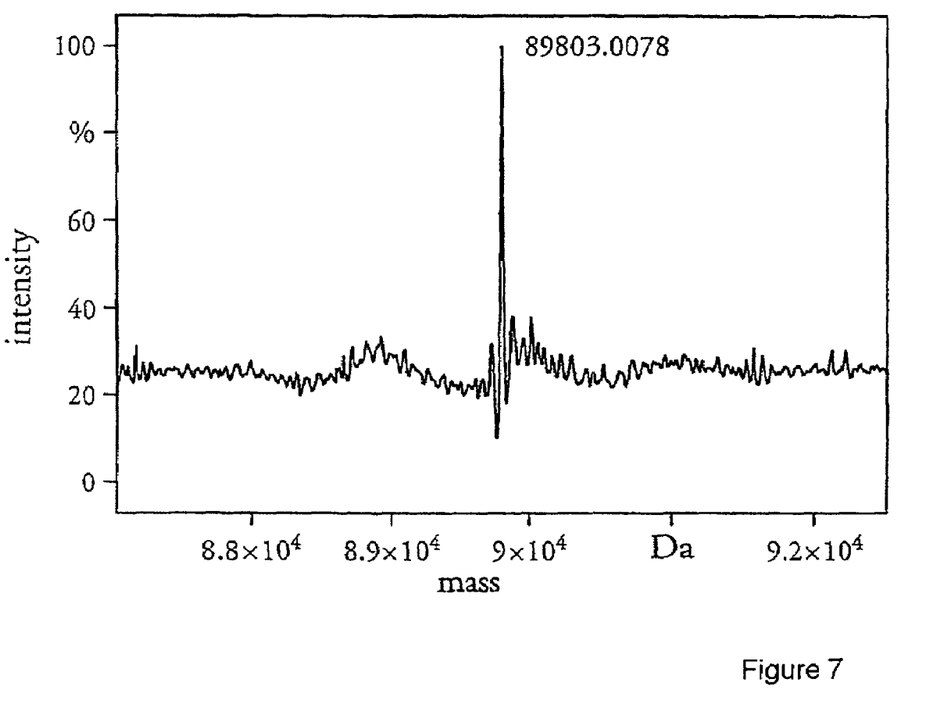
FIG. 7 depicts a MALDI-TOF mass spectrogram, in each case of drBMP-2

MALDI-TOF Mass Spectrometry and N-terminal Sequence Analysis apparent molecular mass: 89803.0078 Da—see FIG. 7
calculated molecular mass (without the starting methionine): 89801.2 Da Biological Activity of rh-proBMP-2 and Rh-drBMP-2

The osteoinductive activity of the modified rh-proBMP-2 and rh-drBMP-2 proteins was examined in an ectopic bone induction model using small laboratory animals. For this, defined quantities of the given factor to be tested (40-200 µg; drBMP-2 or proBMP-2) were applied, after having been sterilized by filtration, to sterile cubiform, chemically and pharmacologically inert ceramic implant bodies of β-TCP.

| Implant specifications: | |
|---|---|
| Manufacturer | Mathys, Bettlach, Switzerland |
| Trade name | chronOs |
| Phase purity | >95% β-TCP |
| Pore volume fraction | 72 +/− 6% |
| Pore size | 80-650 µm |
| Pore structure | interconnecting |
| Solidity | 7.7 +/− 1.2 MPa |

Figure 9:
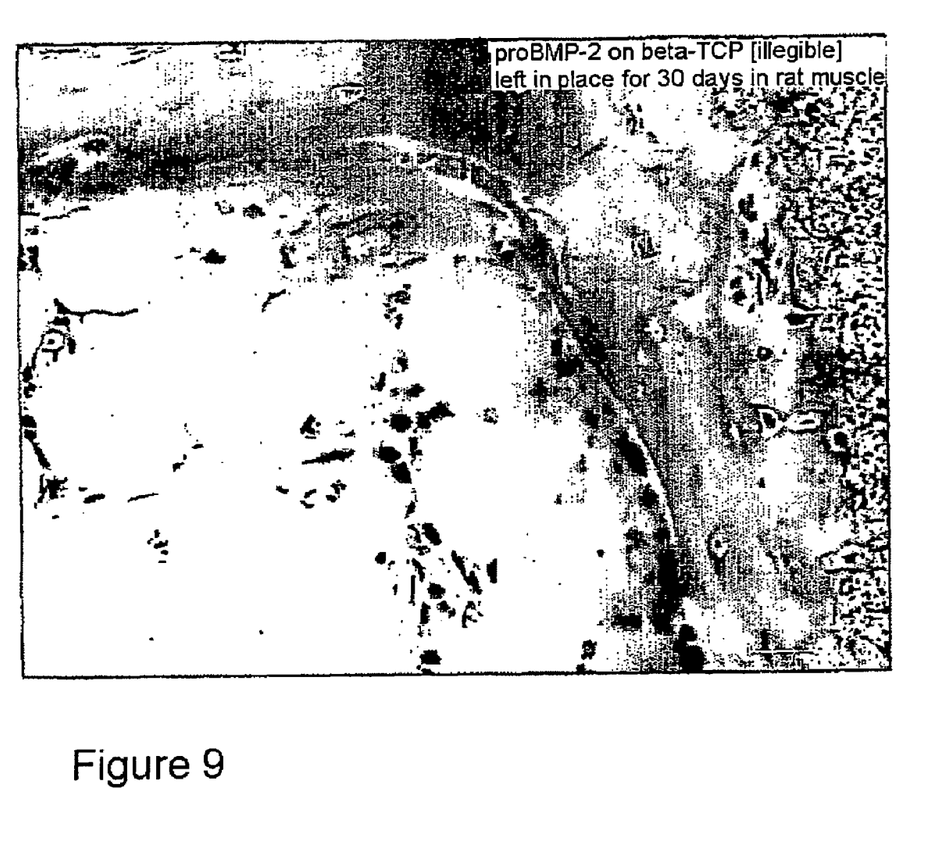
FIG. 9 depicts a histological section of an rh-proBMP-2 implant at high magnification. The bone material (top left to bottom right, light blue) is in very close contact with the ceramic material which it covers (on the right, grey). Active osteoblasts are present in a row between bone substance and hematopoetic tissue.

The factor-coated implants, and also uncoated but otherwise identically treated control implants, were implanted in the anterior abdominal wall musculature of 8 fully grown laboratory rats. For this, several approx. 1 cm-long surgical incisions were made in the skin, and the uppermost muscle layer lying below it, after the rats had been anesthetized. Blunt preparation was used to produce a cavity between the two oblique layers of abdominal musculature, after which the implants were introduced into this cavity and the wounds were closed with surgical sutures. After the implants had been left in place for 30 days, the animals were sacrificed and the implants, together with the surrounding tissue, were removed and examined macroscopically and histologically for bone neoformation. In the case of all the factor-coated implants, it was possible histologically to clearly observe bone neoformation accompanied by the formation of hematopoietically active bone marrow (see FIGS. 8 and 9). Consequently, the biological activity was 100% in the case of both factors (16/16 in the case of proBMP-2; 8/8 in the case of drBMP-2). It was consequently possible to unambiguously provide evidence of osteoinductive activity by the formation of bone tissue in muscle tissue, which is not normally capable of forming bone. It was not possible to observe any qualitative differences in the histological result between proBMP-2 and mature drBMP-2. In no case did the control implants lead to any bone neoformation. Instead of this, they were only enclosed in connective tissue.

Figure 10:
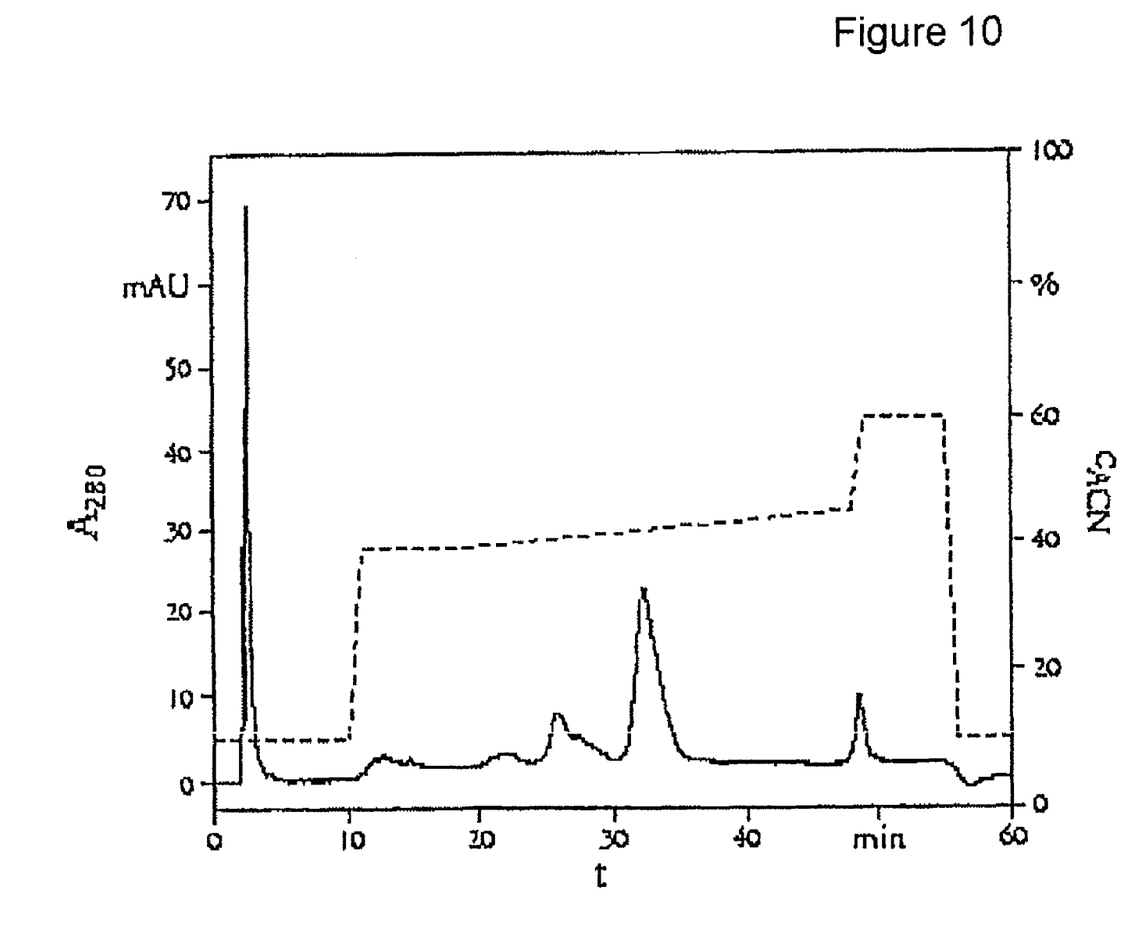
FIG. 10 depicts an RP-HPLC diagram of rh-proBMP-2
Figure 11:
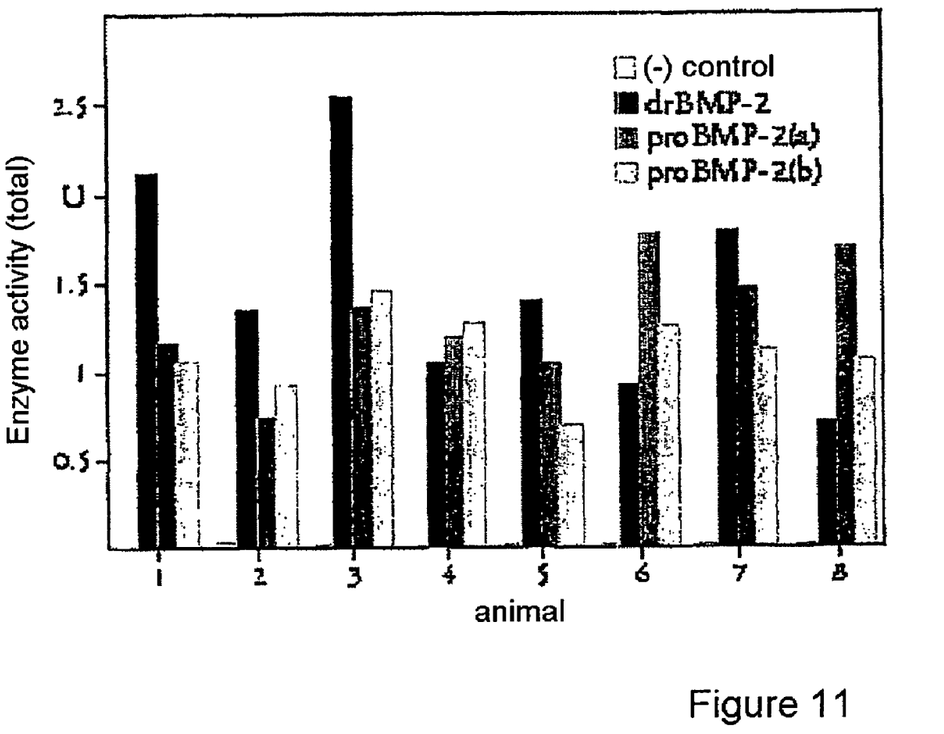
FIG. 11 depicts a comparison of the activity of AP in the implants.

Further evidence of the neoformation of active bone tissue under the influence of rh-proBMP-2 or rh-drBMP-2 was furnished by measuring the activity of alkaline phosphatase (AP) in the implants. To do this, half of each implant was deep-frozen immediately after explantation and stored at −80° C. For extracting the alkaline phosphatase and determining its enzymic activity, the implants were thawed and disrupted in 0.1 M tris/HCl, 1% Triton X-100, pH 7.4 (at 4° C.) using a Potter S homogenizer (B. Braun Biotech), and insoluble constituents were separated off by centrifugation. The clear supernatant was then used for determining the alkaline phosphatase activity using the Ecoline 25 (Merck) test kit. The concentration of the 4-nitrophenol which was liberated in this test was monitored for 5 min at 25° C. and λ=405 nm and the enzymic activity was calculated using equation 1

$$\text{Act.}: \frac{Vb + Vs \cdot \Delta E \cdot 1000}{\varepsilon \cdot Vs \cdot dt} \tag{1}$$

where Vb is the volume of the buffer (1 ml) and Vs is that of the sample (25 ml). In conformity with the manufacturer's instructions, $\varepsilon=18\,518\,l\times mol^{-1}\times cm^{-1}$ was assumed to be the molar absorption coefficient of 4-nitrophenol. The units of the resulting activity are $\mu mol \times min^{-1} \times ml^{-1}$. The results of the test are summarized in Table 1 and FIG. 10. While the enzymic activity in the rh-pro/drBMP-2-containing samples is significantly increased as compared with the (−) controls, that of the rh-drBMP-2 samples is only slightly increased as compared with that of the samples containing rh-proBMP-2 and not in every case, either (exceptions: animals 4, 6 and 8). Taking into consideration the different molecular weights of rh-proBMP-2 (approx. 45 kDa) and rh-drBMP-2 (approx. 12 kDA) and also the fact that the rh-proBMP-2 samples were not used in purified form, and consequently still contained incorrectly folded, monomeric species in a proportion of up to 10%, it can be concluded that, in this animal model, rh-proBMP-2 possesses a bone neoformation-inducing activity which is comparable to that of the (truncated) mature form of the protein.

TABLE 1

Comparison of the alkaline phosphatase activity (in U) in the β-TCP implants coated with drBMP-2 or proBMP-2

| Animal | Control | drBMP-2 | proBMP-2(a) | proBMP-2(b) |
|---|---|---|---|---|
| 1 | 0.0009 | 2.1162 | 1.1654 | 1.049 |
| 2 | 0.0232 | 1.3459 | 0.7443 | 0.9126 |
| 3 | 0.017 | 2.5307 | 1.3521 | 1.4508 |
| 4 | 0.0036 | 1.0461 | 1.1934 | 1.262 |
| 5 | 0.0118 | 1.3884 | 1.0472 | 0.6895 |
| 6 | 0.0142 | 0.9195 | 1.7609 | 1.257 |
| 7 | 0.0112 | 1.776 | 1.4601 | 1.1126 |
| 8 | 0.0149 | 0.7044 | 1.6968 | 1.053 |

Implementation Example 2

Obtaining Biologically Active drBMP-2

Limited Proteolysis of rh-proBMP-2

For the preparative proteolysis of rh-proBMP-2, 50 ml of the renatured protein were dialyzed against 0.1 M tris/HCl pH 7.0, 4 M urea, 1 mM EDTA. Aggregates were separated off by centrifugation (75 000 g, 1 h) and the protein concentration was determined spectrophotometrically (1.3 mg/ml). The losses due to the dialysis amounted to 13%. Trypsin (Roche Diagnostics) was used in a ratio of 1:100 (Trypsin:proBMP-2; w/w), and the mixture was incubated at 5-7° C. for 4 h. The trypsin was inactivated with an 8-fold molar excess of soybean trypsin inhibitor (SBTI; Sigma). The entire mixture was dialyzed against urea-free buffer (0.1 M tris/HCl, pH 7.0) in the presence of hydrophobic column material (20 ml of Fractogel-Phenyl, Merck). The column material, which had been loaded with drBMP-2 in this way, was packed into an empty column (XK-16, Pharmacia) and then washed with:

- 5 CV (column volumes) of low salt buffer (dialysis buffer),
- 5 CV of 50 mM Na acetate, pH 5.0,
- 2 CV of 50 mM Na acetate, pH 5.0, 4 M urea, and
- 2 CV of 50 mM Na acetate, pH 5.0, 1 M L-arginine.

The column was eluted with 6 M GdmCl, 0.2 M acetic acid. The drBMP-2-containing fractions were combined and dialyzed against 0.1% TFA. It was not possible to observe any aggregate formation. The dialyzate was sterilized by filtration and the protein concentration was determined spectrophotometrically (1.3 mg/ml). The yield of BMP-2 which was obtained in this way was approx. 50% based on the renaturate which was used for the limited proteolysis. Consequently, approx. 17 mg of biologically active drBMP-2s can be obtained from 1 l of *E. coli* culture or 5.2 (corresponds to 5.6 mg of mature BMP-2 incl. N-terminal heparin-binding site) based on 1 g (wet weight) of induced *E. coli* cells. By contrast, only 0.2 mg of BMP-2 was obtained per 1 g of cells using the method described by Ruppert et al., [Eur. J. Biochem. 237 (1996), 295-302].

Characterizing drBMP-2

Analyzing the Proteolysis Products by Means of N-terminal Sequencing

The N-terminal sequencing [Edman and Begg, Eur. J. Biochem. 1 (1967), 80-91] was carried out after performing SDS-PAGE and Western blotting onto a PVDF membrane. The sequencing gave the following amino acid sequences for drBMP-2 which was generated in accordance with the invention:

a) Leu-Lys-Ser-Ser-Cys-Lys-Arg-
b) Lys-Arg-Leu-Lys-Ser-Ser-Cys-
c) Arg-Leu-Lys-Ser-Ser-Cys-Lys-

The ratio of the different species to each other is about 3:2:1 (a:b:c). While it was not possible to detect the cysteines, it was possible to detect the amino acids which followed them. However, the sequence was completely verified at the DNA level. It corresponds to the N-terminus of mature BMP-2 without the heparin binding site. drBMP-2 was used for the sequencing both in the reduced form and in the nonreduced form. It was only possible to sequence the nonreduced form up to the second serine, suggesting that the following residue is a cystine, that is a constituent of a disulfide bridge. Taken overall, the proteolysis product consequently corresponds to a mature BMP-2 which has been truncated N-terminally by 7-9 amino acids and which therefore lacks the heparin binding site.

Under the limited proteolysis conditions described here, peptide chains which are not disulfide-bridged are degraded, meaning that, in the end, it is only drBMP-2 which is 100% covalently dimerized which is obtained.

Figure 4:
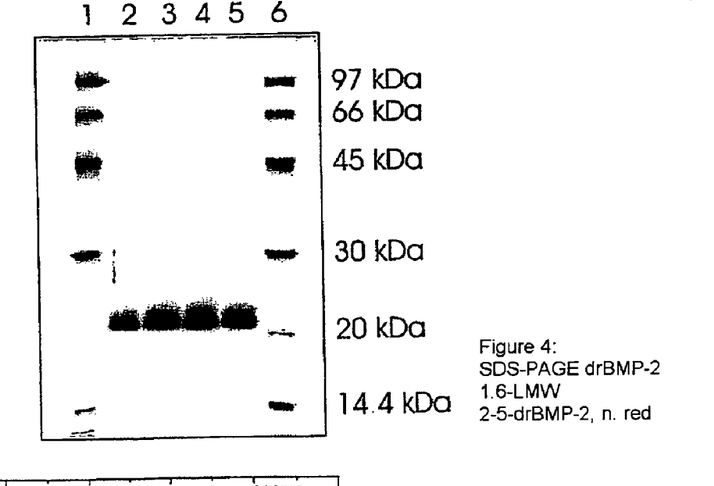
FIG. 4 depicts an SDS-PAGE electropherogram

Analyzing drBMP-2 for Purity Using SDS-polyacrylamide Gel Electrophoresis and HPLC The size and purity of the drBMP-2 which was obtained in accordance with the invention was checked by carrying out SDS-PAGE under reducing and nonreducing conditions and then carrying out silver staining (lanes 6 and 11 in FIG. 4). It is 100% dimerized and is more than 95% pure.

Figure 5:
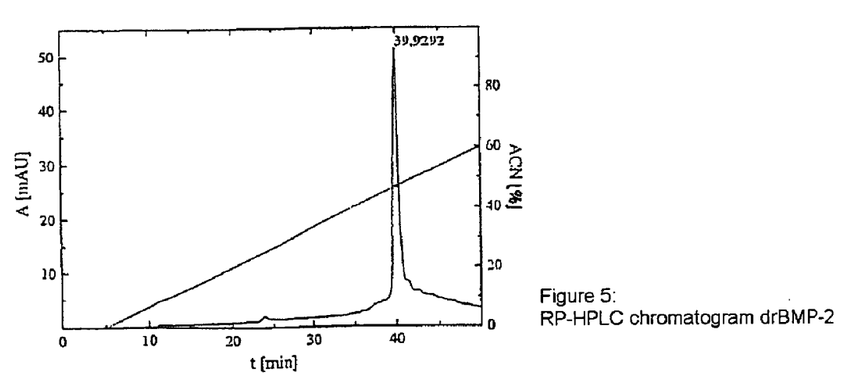
FIG. 5 depicts an RP-HPLC-chromatogram

In addition, reversed-phase high performance liquid chromatography (RP-HPLC; Vydac $C_4$) was used for checking the purity and homogeneity of drBMP-2. In this experiment, drBMP-2 eluted in a homogeneous peak at 46.57% acetonitrile and 0.1% TFA (FIG. 5), providing support for the uniform structuring and, in particular, disulfide-bridging, of the protein.

Circular Dichroism Spectrometry

Figure 6:
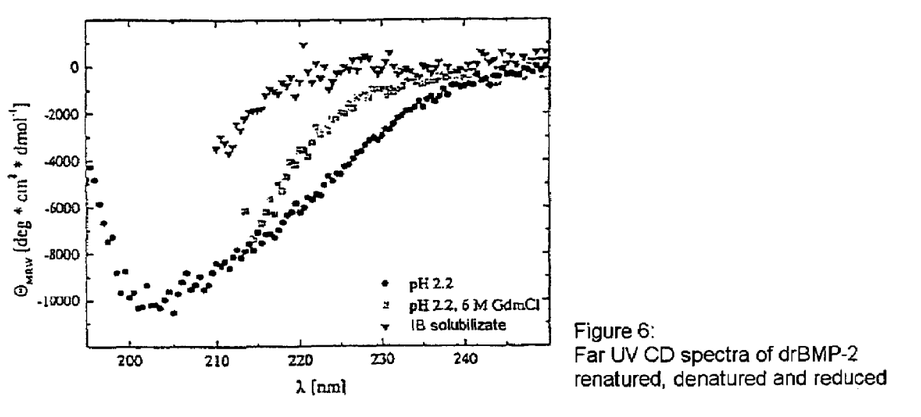
FIG. 6 depicts UV-CD spectra

The marked difference between the ellipticity of renatured and denatured drBMP-2 and, in particular, of reduced and denatured mature BMP-2 (IB solubilizate) in the 210-230 nm region of the far UV CD spectrum (FIG. 6) makes it possible to conclude that, in the process according to the invention for renaturing the proprotein, secondary structure elements are formed in the mature domain of the protein as well.

TABLE 2

Subject: 3 letter code proBMP (incl. 20 AA His tag)

MetGlySerSerHisHisHisHisHisHisSerSerGlyLeuValProArgGlySerHisMetGlyAlaAlaGlyLeuVal

ProGluLeuGlyArgArgLysPheAlaAlaAlaSerSerGlyArgProSerSerGlnProSerAspGluValLeuSerGlu

PheGluLeuArgLeuLeuSerMetPheGlyLeuLysGlnArgProThrProSerArgAspAlaValValProProTyrMet

LeuAspLeuTyrArgArgHisSerGlyGlnProGlySerProAlaProAspHisArgLeuGluArgAlaAlaSerArgAla

AsnThrValArgSerPheHisHisGluGluSerLeuGluGluLeuProGluThrSerGlyLysThrThrArgArgPhePhe

PheAsnLeuSerSerIleProThrGluGluPheIleThrSerAlaGluLeuGlnValPheArgGluGlnMetGlnAspAla

TABLE 2-continued

Subject: 3 letter code proBMP (incl. 20 AA His tag)

LeuGlyAsnAsnSerSerPheHisHisArgIleAsnIleTyrGluIleIleLysProAlaThrAlaAsnSerLysPhePro

ValThrArgLeuLeuAspThrArgLeuValAsnGluAsnAlaSerArgTrpGluSerPheAspValThrProAlaValMet

ArgTrpThrAlaGluGlyHisAlaAsnHisGlyPheValValGluValAlaHisLeuGluGluLysGlnGlyValSerLys

ArgHisValArgIleSerArgSerLeuHisGlnAspGluHisSerTrpSerGlnIleArgProLeuLeuValThrPheGly

HisAspGlyLysGlyHisProLeuHisLysArgGluLysArgGlnAlaLysHisLysGlnArgLysArgLeuLysSerSer

CysLysArgHisProLeuTyrValAspPheSerAspValGlyTrpAsnAspTrpIleValAlaProProGlyTyrHisAla

PheTyrCysHisGlyGluCysProPheProLeuAlaAspHisLeuAsnSerThrAsnHisAlaIleValGlnThrLeuVal

AsnSerValAsnSerLysIleProLysAlaCysCysValProThrGluLeuSerAlaIleSerMetLeuTyrLeuAspGlu

AsnGluLysValValLeuLysAsnTyrGlnAspMetValValGluGlyCysGlyCysArg

---

The invention claimed is:

1. A method for promoting bone healing or producing bone replacement material or implants comprising administering to a subject in need thereof a therapeutically effective amount of recombinantly generated pro-BMP-2 wherein said pro-BMP-2 consists of an amino acid sequence which is (i) amino acids 22-284 of SEQ ID NO: 7, concatenated to (ii) amino acids 285-398 of SEQ ID NO: 7.

2. A composition for promoting bone growth comprising recombinantly generated pro-BMP-2, wherein said pro-BMP-2 consists of an amino acid sequence which is (i) amino acids 22-284 of SEQ ID NO: 7, concatenated to (ii) amino acids 285-398 of SEQ ID NO: 7, and a pharmaceutically acceptable carrier.

3. A method for promoting bone growth comprising administering to a subject in need thereof a therapeutically effective amount of recombinantly generated pro-BMP-2, wherein said pro-BMP-2 consists of an amino acid sequence which is (i) amino acids 22-284 of SEQ ID NO: 7, concatenated to (ii) amino acids 285-398 of SEQ ID NO:7.

4. The method of claim 3, wherein said pro-BMP-2 is administered in the form of a preparation comprising a physiologically tolerated support material which is coated or impregnated with the pro-BMP-2.

* * * * *

SEQUENCE LISTING

<160> NUMBER OF SEQ ID NOS: 7

<210> SEQ ID NO 1
<211> LENGTH: 34
<212> TYPE: DNA
<213> ORGANISM: Artificial Sequence
<220> FEATURE:
<221> NAME/KEY: CDS
<222> LOCATION: (12)..(32)
<223> OTHER INFORMATION: description of artificial sequence: forward
      primer FwProBMP

<400> SEQUENCE: 1
cggaattcca t atg ggt gcg gct ggc ctc gtt cc                              34
            Met Gly Ala Ala Gly Leu Val
             1               5

<210> SEQ ID NO 2
<211> LENGTH: 7
<212> TYPE: PRT
<213> ORGANISM: Artificial Sequence
<220> FEATURE:
<223> OTHER INFORMATION: description of artificial sequence: forward
      primer FwProBMP

<400> SEQUENCE: 2

Met Gly Ala Ala Gly Leu Val
 1               5

<210> SEQ ID NO 3
<211> LENGTH: 29
<212> TYPE: DNA
<213> ORGANISM: Artificial Sequence
<220> FEATURE:
<223> OTHER INFORMATION: description of artificial sequence: reverse
      primer RevBMP

<400> SEQUENCE: 3
ccggatcctt actagcgaca cccacaacc                                          29

<210> SEQ ID NO 4
<211> LENGTH: 7
<212> TYPE: PRT
<213> ORGANISM: Artificial Sequence

```
<220> FEATURE:
<223> OTHER INFORMATION: description of artificial sequence: proteolysis
      products

<400> SEQUENCE: 4

Leu Lys Ser Ser Cys Lys Arg
1               5

<210> SEQ ID NO 5
<211> LENGTH: 7
<212> TYPE: PRT
<213> ORGANISM: Artificial Sequence
<220> FEATURE:
<223> OTHER INFORMATION: description of artificial sequence: proteolysis
      products

<400> SEQUENCE: 5

Lys Arg Leu Lys Ser Ser Cys
1               5

<210> SEQ ID NO 6
<211> LENGTH: 7
<212> TYPE: PRT
<213> ORGANISM: Artificial Sequence
<220> FEATURE:
<223> OTHER INFORMATION: description of artificial sequence: proteolysis
      products

<400> SEQUENCE: 6

Arg Leu Lys Ser Ser Cys Lys
1               5

<210> SEQ ID NO 7
<211> LENGTH: 398
<212> TYPE: PRT
<213> ORGANISM: Artificial Sequence
<220> FEATURE:
<223> OTHER INFORMATION: description of artificial sequence: proBMP

<400> SEQUENCE: 7

Met Gly Ser Ser His His His His His Ser Ser Gly Leu Val Pro
1               5                   10                  15

Arg Gly Ser His Met Gly Ala Ala Gly Leu Val Pro Glu Leu Gly Arg
                20                  25                  30

Arg Lys Phe Ala Ala Ala Ser Ser Gly Arg Pro Ser Ser Gln Pro Ser
            35                  40                  45

Asp Glu Val Leu Ser Glu Phe Glu Leu Arg Leu Leu Ser Met Phe Gly
    50                  55                  60

Leu Lys Gln Arg Pro Thr Pro Ser Arg Asp Ala Val Val Pro Pro Tyr
65                  70                  75                  80

Met Leu Asp Leu Tyr Arg Arg His Ser Gly Gln Pro Gly Ser Pro Ala
                85                  90                  95

Pro Asp His Arg Leu Glu Arg Ala Ala Ser Arg Ala Asn Thr Val Arg
            100                 105                 110

Ser Phe His His Glu Glu Ser Leu Glu Glu Leu Pro Glu Thr Ser Gly
        115                 120                 125

Lys Thr Thr Arg Arg Phe Phe Phe Asn Leu Ser Ser Ile Pro Thr Glu
    130                 135                 140

Glu Phe Ile Thr Ser Ala Glu Leu Gln Val Phe Arg Glu Gln Met Gln
145                 150                 155                 160

Asp Ala Leu Gly Asn Asn Ser Ser Phe His His Arg Ile Asn Ile Tyr
                165                 170                 175
```

-continued

```
Glu Ile Ile Lys Pro Ala Thr Ala Asn Ser Lys Phe Pro Val Thr Arg
            180             185             190

Leu Leu Asp Thr Arg Leu Val Asn Gln Asn Ala Ser Arg Trp Glu Ser
        195             200             205

Phe Asp Val Thr Pro Ala Val Met Arg Trp Thr Ala Gln Gly His Ala
    210             215             220

Asn His Gly Phe Val Val Glu Val Ala His Leu Glu Glu Lys Gln Gly
225             230             235             240

Val Ser Lys Arg His Val Arg Ile Ser Arg Ser Leu His Gln Asp Glu
            245             250             255

His Ser Trp Ser Gln Ile Arg Pro Leu Leu Val Thr Phe Gly His Asp
            260             265             270

Gly Lys Gly His Pro Leu His Lys Arg Glu Lys Arg Gln Ala Lys His
            275             280             285

Lys Gln Arg Lys Arg Leu Lys Ser Ser Cys Lys Arg His Pro Leu Tyr
        290             295             300

Val Asp Phe Ser Asp Val Gly Trp Asn Asp Trp Ile Val Ala Pro Pro
305             310             315             320

Gly Tyr His Ala Phe Tyr Cys His Gly Glu Cys Pro Phe Pro Leu Ala
            325             330             335

Asp His Leu Asn Ser Thr Asn His Ala Ile Val Gln Thr Leu Val Asn
            340             345             350

Ser Val Asn Ser Lys Ile Pro Lys Ala Cys Cys Val Pro Thr Glu Leu
        355             360             365

Ser Ala Ile Ser Met Leu Tyr Leu Asp Glu Asn Glu Lys Val Val Leu
        370             375             380

Lys Asn Tyr Gln Asp Met Val Val Glu Gly Cys Gly Cys Arg
385             390             395
```